(12) United States Patent
Takei et al.

(10) Patent No.: US 10,617,462 B2
(45) Date of Patent: Apr. 14, 2020

(54) MEDICAL DEVICE

(71) Applicant: OLYMPUS CORPORATION, Tokyo (JP)

(72) Inventors: Yusuke Takei, Hino (JP); Tomoyuki Takashino, Fuchu (JP); Kazuhiro Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 284 days.

(21) Appl. No.: 15/260,408

(22) Filed: Sep. 9, 2016

(65) Prior Publication Data

US 2017/0065325 A1    Mar. 9, 2017

Related U.S. Application Data

(63) Continuation of application No. PCT/JP2016/063912, filed on May 10, 2016.

(30) Foreign Application Priority Data

Sep. 9, 2015    (JP) ................................. 2015-177503

(51) Int. Cl.
*A61B 18/04* (2006.01)
*A61B 18/08* (2006.01)
(Continued)

(52) U.S. Cl.
CPC .... *A61B 18/085* (2013.01); *A61B 17/320068* (2013.01); *A61B 18/1445* (2013.01);
(Continued)

(58) Field of Classification Search
CPC ........ A61B 18/085; A61B 2018/00095; A61B 2018/00101
See application file for complete search history.

(56) References Cited

U.S. PATENT DOCUMENTS

2002/0107517 A1\* 8/2002 Witt .................... A61B 18/1442
606/50
2003/0187429 A1\* 10/2003 Karasawa ............ A61B 18/085
606/28
(Continued)

FOREIGN PATENT DOCUMENTS

JP       2003-275220 A     9/2003
JP       2007-37568 A      2/2007
(Continued)

OTHER PUBLICATIONS

International Preliminary Report on Patentability dated Mar. 22, 2018 received in International Application No. PCT/JP2016/063912.
(Continued)

*Primary Examiner* — Daniel W Fowler
(74) *Attorney, Agent, or Firm* — Scully, Scott, Murphy & Presser, P.C.

(57) ABSTRACT

A medical device that includes a support member, a heat insulator provided on at least a portion of a first surface of the support member, an energy output member configured to output energy, the energy output member provided on at least a portion of a first surface of the heat insulator, the output energy configured to treat biological tissue and a heat conductor provided on at least a portion of the first surface of the support member and contacting a second surface of the heat insulator, the second surface of the heat insulator opposite the first surface of the heat insulator, wherein a portion of the support member is located proximal than the energy output, and the energy output member is configured to transfer heat to the heat insulator, and wherein the heat conductor is configured to conduct the heat from the heat insulator to the support member.

14 Claims, 8 Drawing Sheets

(51) Int. Cl.
*A61B 18/00* (2006.01)
*A61B 18/14* (2006.01)
*A61B 17/32* (2006.01)

(52) U.S. Cl.
CPC ............... *A61B 2018/00005* (2013.01); *A61B 2018/00095* (2013.01); *A61B 2018/00101* (2013.01); *A61B 2018/00107* (2013.01)

(56) References Cited

U.S. PATENT DOCUMENTS

| | | | | |
|---|---|---|---|---|
| 2004/0087943 | A1* | 5/2004 | Dycus | A61B 17/2909 606/51 |
| 2005/0004568 | A1* | 1/2005 | Lawes | A61B 18/14 606/51 |
| 2005/0107785 | A1* | 5/2005 | Dycus | A61B 18/1445 606/51 |
| 2005/0203499 | A1* | 9/2005 | Pendekanti | A61B 17/320092 606/27 |
| 2006/0217709 | A1* | 9/2006 | Couture | A61B 18/1442 606/51 |
| 2009/0299353 | A1* | 12/2009 | Lewinsky | A61B 17/295 606/16 |
| 2011/0306967 | A1* | 12/2011 | Payne | A61B 18/1445 606/41 |
| 2012/0330308 | A1* | 12/2012 | Joseph | A61B 18/1442 606/45 |
| 2013/0035685 | A1 | 2/2013 | Fischer et al. | |
| 2013/0226178 | A1 | 8/2013 | Brandt et al. | |
| 2014/0088463 | A1* | 3/2014 | Wolf | A61F 5/08 601/2 |
| 2015/0148832 | A1 | 5/2015 | Boudreaux et al. | |
| 2015/0297289 | A1 | 10/2015 | Hirai et al. | |

FOREIGN PATENT DOCUMENTS

| | | |
|---|---|---|
| JP | 2008-534068 A | 8/2008 |
| WO | WO 2014/196641 A1 | 12/2014 |

OTHER PUBLICATIONS

Japanese Office Action dated Jul. 4, 2017 received in Japanese Patent Application No. 2017-522700, together with an English-language translation.
International Search Report dated Aug. 9, 2016 received from International Application No. PCT/JP2016/063912.
Extended Supplementary European Search Report dated Mar. 7, 2019 received in European Patent Application No. 16 84 3986.7.

* cited by examiner

MEDICAL DEVICE

CROSS-REFERENCE TO RELATED APPLICATIONS

This application is a Continuation Application of PCT International Application No. PCT/JP2016/063912, filed on May 10, 2016, and claims the benefit of priority from prior Japanese Patent Application No. 2015-177503, filed on Sep. 9, 2015. The entire contents of PCT International Application No. PCT/JP2016/177503 and Japanese Patent Application No. 2015-177503 are incorporated herein by reference.

TECHNICAL FIELD

The present invention relates to a medical device for treating biological, tissue using energy such as heat.

BACKGROUND ART

Surgical devices for cutting and sealing a blood vessel can include a jaw for sandwiching and fastening tissue, sealing the tissue by heat or the like. In other surgical devices a pair of jaws are included, each of which include a heating element. When grasped, the jaws generate heat from each element to perform an operation, such as a coagulation of the biological tissue or incising the biological tissue.

SUMMARY OF THE INVENTION

Problems to be Solved by the Invention

There, has been demand for more minimally invasive, medical devices, to reduce the burden on patients.

Means for Solving the Problem

To achieve the object stated above, a medical device according to one aspect of the present invention includes: a support member; a heat insulator provided on at least a portion of a first surface of the support member; an energy output member configured to output energy, the energy output member provided on at least a portion of a first surface of the heat insulator, the output energy configured to treat biological tissue; and a heat conductor provided on at least a portion of the first surface of the support member and contacting a second surface of the heat insulator, the second surface of the heat insulator opposite the first surface of the heat insulator, wherein: a portion of the support member is located proximal than the energy output, and the energy output member is configured to transfer heat to the heat insulator, and wherein the heat conductor is configured to conduct the heat from the heat insulator to the support member.

Advantageous Effect of the Invention

With the structure described above, a more minimally invasive medical device can be provided.

MODE FOR CARRYING OUT THE INVENTION

The following describes a medical device according to an embodiment, with reference to FIGS. 1 to 6.

Figure 1:
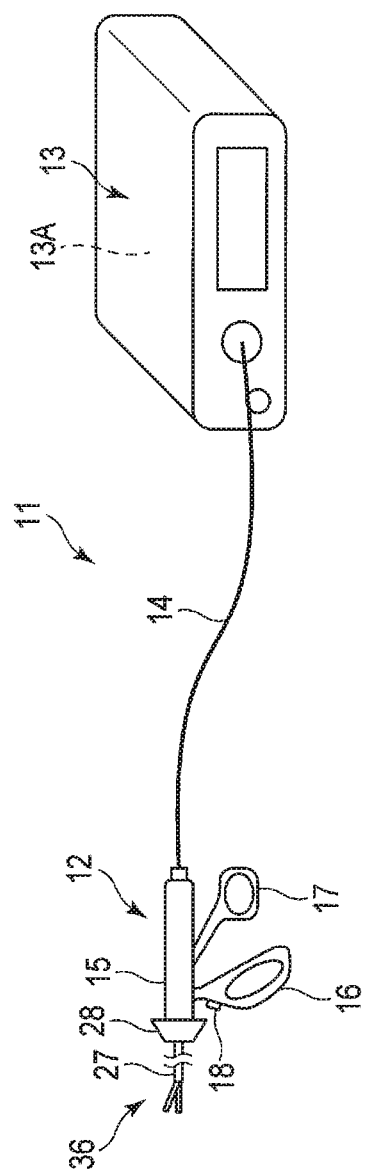
FIG. 1 is a schematic view illustrating the overall structure of a medical device according to an embodiment.

As illustrated in FIG. 1, a medical device 11 includes a handpiece 12, a power unit 13, and a cable 14 connecting the handpiece 12 and the power unit 13.

As illustrated in FIG. 1, the handpiece 12 includes: a case 15 forming an outer envelope; a fixed handle 16 formed integrally with the case 15; a handle 17 rotatable with respect to the case 15; and an operation button 18 provided on the case 15. Although the number of operation buttons 18 is one in this embodiment, a plurality of operation buttons 18 may be provided.

As illustrated in FIGS. 1, the handpiece 12 includes: an end effector 36 for treating biological tissue; a sheath 27 configured to extend from the case 15; and a rotatable knob 28 fixed to the below-mentioned sheath 27.

Figure 2:
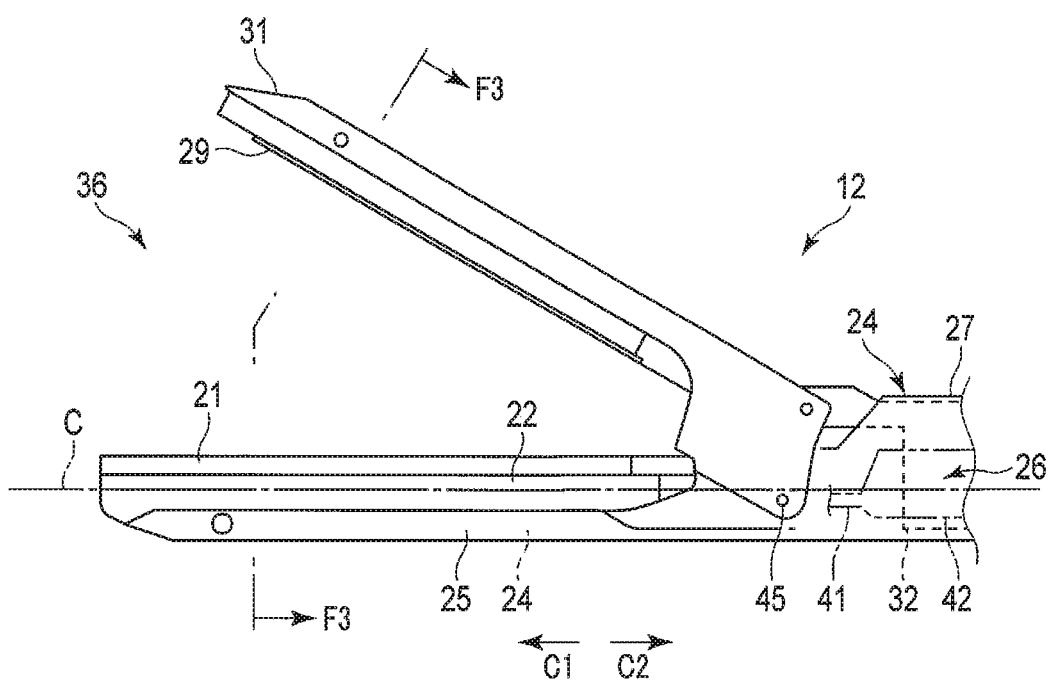
FIG. 2 is a side view illustrating an energy output member and jaw of a handpiece in the medical device illustrated in FIG. 1.

In this embodiment, referring to FIG. 2, one of the two directions parallel to the central axis direction (longitudinal direction) C of the sheath 27 is referred to as the distal direction C1, and the direction opposite to the distal direction as the proximal direction C2. As illustrated in FIG. 2, the energy output member 21 (first grasping piece 21) and the jaw 31 (second grasping piece 31) constitute an end effector 36 for treating the site of the treatment object.

As illustrated in FIG. 2, the end effector 36 includes an energy output member 21 configured to output energy for treating biological tissue; a heat insulator 22 fixed to the energy output member 21; a support member 23 configured to support the energy output member 21 and the heat insulator 22; a heat-insulation cover 25 configured to cover the below-mentioned housing 24 of the support member 23; a heat conductor 26 configured to extend over the heat insulator 22 and the support member 23; a jaw 31 attached to the sheath 27 rotatably with respect to the energy output member 21; a pad 29 provided on the jaw 31; and a cylindrical movable pipe 32 placed inside the sheath 27 and configured to move forward and backward when the jaw 31 is opened and closed. The support member 23 includes: the sheath 27 shaped like a cylindrical pipe, the sheath 27 can be formed of any suitable material such as a metal containing material; and the housing 24 fixed to the distal side of the sheath 27 through a screw, welding, or the like.

Figure 3:
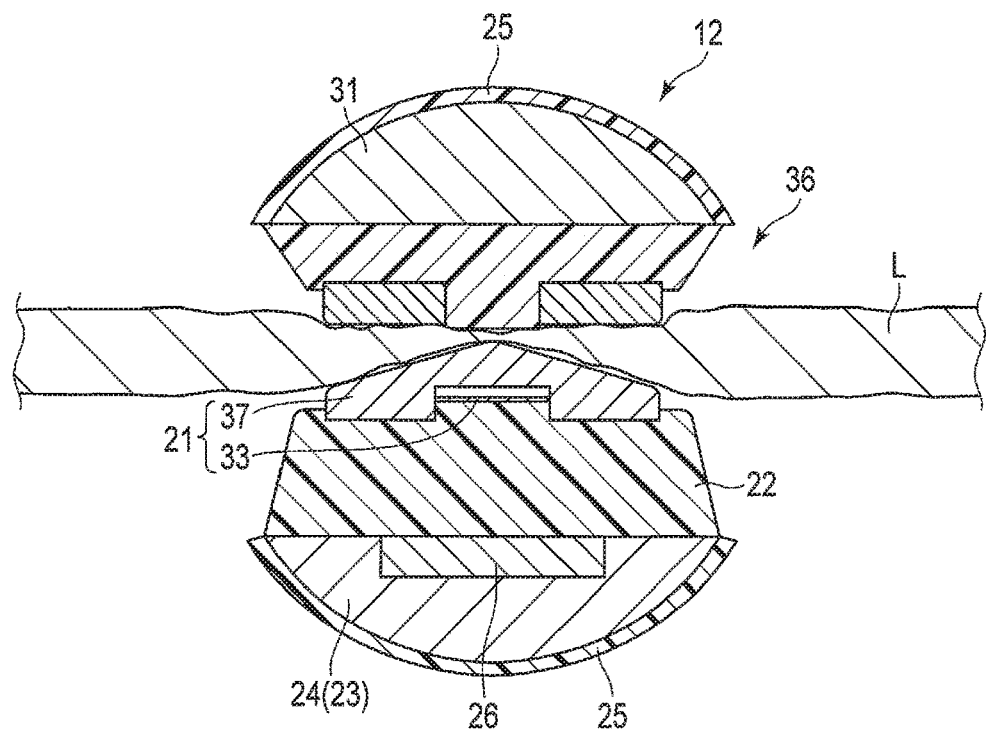
FIG. 3 is a sectional view of the handpiece along line F3-F3 in FIG. 2.
Figure 4:
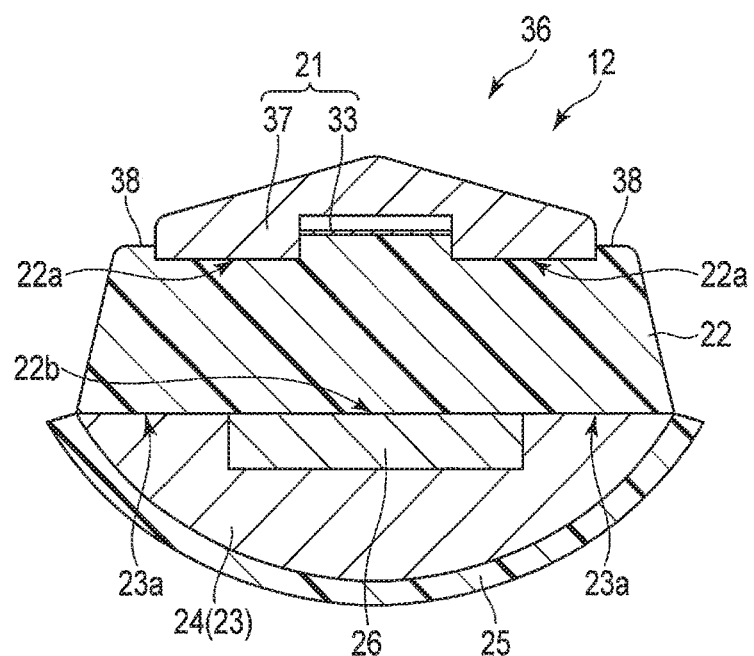
FIG. 4 is an enlarged sectional view illustrating the energy output member, heat insulator, and housing of the handpiece illustrated in FIG. 3.

As illustrated in FIG. 3, the jaw 31 is configured to be opened and closed to release or squeeze the biological tissue L between the energy output member 21 and the jaw 31. Energy output member 21 includes contact section 37 (blade) configured to have an angular cross-section; and the heater 33 (heater element) housed inside the contact section 37. The surface of the contact section 37 can include a coating, such as a fluororesin or the like, to limit biological tissue L (as shown in FIG. 4) from sticking to the contact section 37. The contact section 37 can be configured to have an angular cross-section.

As illustrated in FIG. 4, the heat insulator 22 is provided on at least a portion of a first surface 23a of the support member 23. The energy output member 21 is provided on at least a portion of a first surface 22a of the heat insulator 22. In this embodiment, the heat conductor 26 contacts a second surface 22b of the heat insulator 22, the second surface 22b of the heat insulator 22 opposite the first surface 22a of the heat insulator 22.

Figure 5:
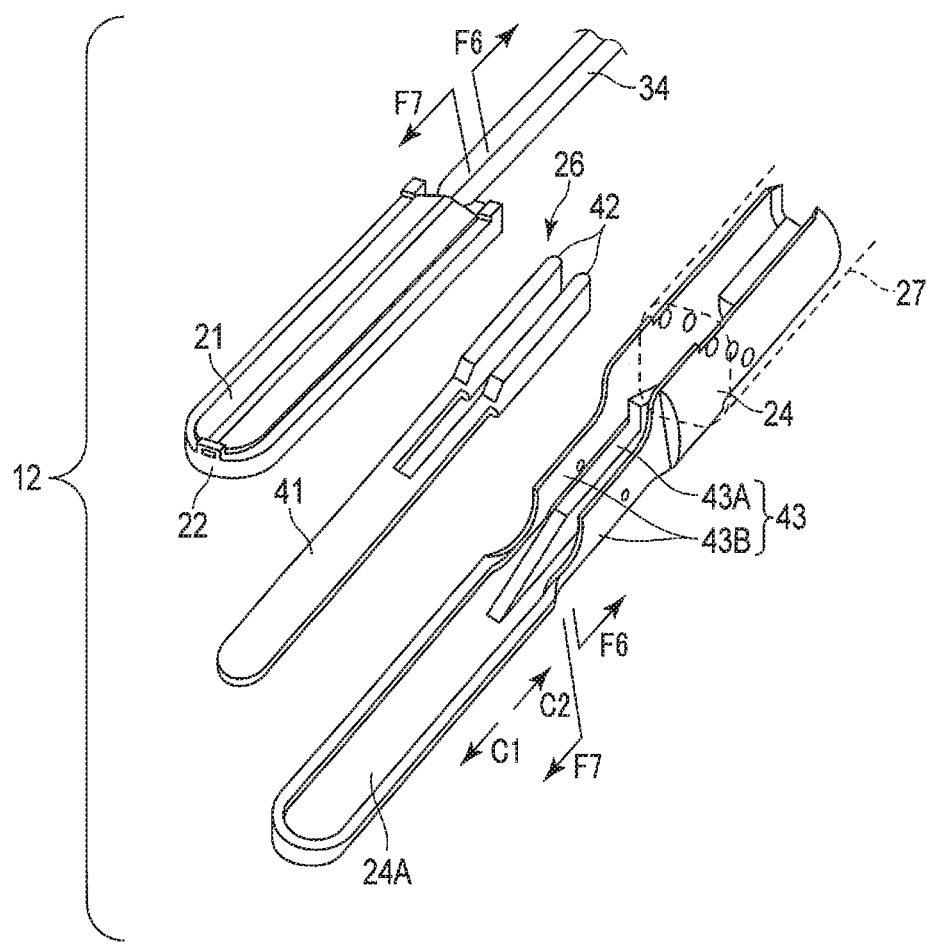
FIG. 5 is an exploded perspective view illustrating the energy output member, heat conductor, and housing in the support member illustrated in FIG. 4.

As illustrated in FIGS. 5, the housing 24 includes a projection section 24A configured to project from the housing 24. The heat conductor 26, the heat insulator 22, and the energy output member 21 can be fixed to the projection section 24A. The housing 24 (including the projection section 24A) is adjacent to the heat insulator 22. The outer periphery of the housing 24 is covered with the heat-insulation cover 25. The cover 25 is made, of a synthetic resin material such as polyether ether ketone (PEEK). Alternatively, the cover 25 may be made of polytetrafluoroethylene (PTFE), tetrafluoroetylene-perfluoroalkylvinylether copolymer (PFA), polyimide (PI), polybenzimidazole (PBI), or the like, or made of ceramic.

Figure 6:
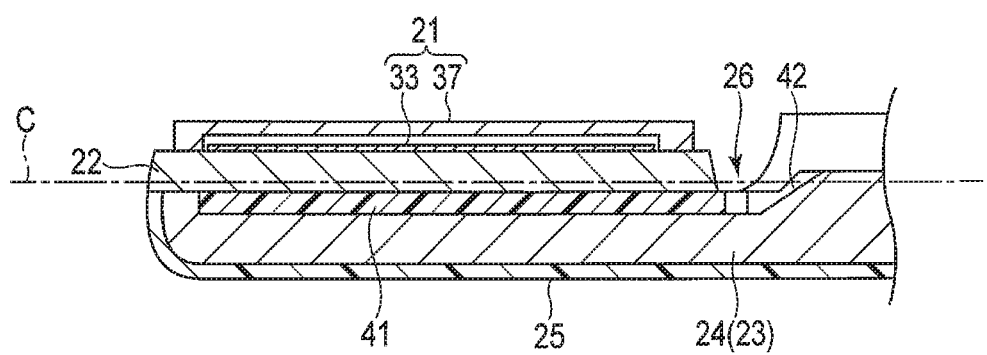
FIG. 6 is a sectional view illustrating an energy output member, a body portion of the heat conductor, housing, and the heat insulator illustrated in FIG. 5.

As illustrated in FIG. 6, the energy output member 21 includes: a contact section 37 (blade) configured to extend in the central axis direction C of the sheath 27 and having an angular cross-section; and the heater 33 (heater element) housed inside the contact section 37. The contact section 37 is a part that comes into direct contact with the treatment object. The heater 33 is located between the contact section 37 and the heat insulator 22, and can impart heat energy to the contact section 37. For example, the heater 33 is composed of resistors using stainless steel, a nickel-chromium alloy (nichrome wire), or the like. The contact section 37 is made of a metal having good heat conductivity, such as a copper alloy or an aluminum alloy.

As illustrated in FIG. 4, the heat insulator 22 is shown as a trapezoidal shape, but in other embodiments can be any other suitable shape such as square, triangular, etc. The heat insulator 22 supports the energy output member 21 on its top surface. The heat insulator 22 is fixed to the housing 24 in FIG. 4, but in other embodiments, the heat insulator 22 can be fixed to other portions of the housing 24(the support member 23). The heat insulator 22 includes an outer edge section 38 (step section), which has a fixed width dimension along the outer periphery of the energy output member 21. The outer edge section 38 projects more outward than the outer periphery of the energy output member 21. The medical device 11 according to this embodiment therefore has lower risk of erroneously bringing the energy output member 21 into contact with biological tissue around the site of the treatment object.

For example, the heat insulator 22 is made of a synthetic resin material. In more detail, the heat insulator 22 is made of PEEK or the like. The material of the heat insulator 22 is, however, not limited to such. The heat insulator 22 may be made of a synthetic resin material other than PEEK, such as PTFE, PFA, PI, or PEI, or made of ceramic with low heat conductivity, etc. The heat insulator 22 has sufficiently lower heat conductivity than metal, etc., and so exhibits heat insulation property to insulate heat of the energy output member 21 transferring to the housing 24.

As illustrated in FIG. 4, the heat conductor 26 is housed in a depression formed in the housing 24. The heat conductor 26 is located between the heat insulator 22 and the housing 24.

As illustrated in FIG. 5, the heat conductor 26 includes a body section 41 (heat conduction section) and a heatsink section 42 at the end of the body section 41. The heatsink section 42 is formed as a pair of blocks or masses configured to extend in the direction (vertical direction) intersecting the treatment surface of the contact section 37. As illustrated in FIG. 6, the heat conductor 26 includes a part of the support member 23 more proximal than the energy output member 21. The heatsink section 42 is opposite to the end adjacent to the heat insulator 22. The heat conductor 26 is made of a metal containing material having good heat conductivity, such as copper or aluminum.

The total volume of the two parts of the heatsink section 42 can be equal to or larger than the volume of the body section 41. In some embodiments heatsink section 42 can be between 0% and 100%, such as 10% larger than the volume of the body section, 20% larger than the body section, 30% larger than the body section, or an even larger percentage. Moreover, the total cross-sectional area of the two parts of the heatsink section 42 along a plane intersecting the direction in which the body section 41 extends can be larger than the cross-sectional area of the body section 41 along a plane parallel to the plane.

The housing 24 forms the outer envelope of the end effector 36, and supports the energy output member 21 with the heat insulator 22 in between. The housing 24 is made of a suitable metal containing material such as stainless steel. The housing 24 therefore has lower heat conductivity than the heat conductor 26.

As illustrated in FIG. 5, the housing 24 includes an engaging section 43 whose shape is complementary to the shape of the heatsink section 42 of the heat conductor 26. In detail, the engaging section 43 includes: a rib section 43A sandwiched between the pair of blocks of the heatsink section 42; and a wall section 43B configured to hold the periphery of the blocks. Thus, the housing 24 is thermally connected to the heatsink section 42, to receive heat transferred to the heatsink section 42 and conduct the heat toward the sheath 27.

As illustrated in FIG. 2, the sheath 27 is shaped like a rod, and supports the housing 24 on the distal side. As illustrated in FIG. 1, the sheath 27 is attached to the case 15 rotatably with respect to the case 15, at its proximal part. The rotatable knob 28 is fixed to the sheath 27. By rotating the rotatable knob 28 with respect to the case 15, the sheath 27, the energy output member 21, and the jaw 31 can be rotated integrally about the central axis C. The sheath 27 has a support pin 45 for supporting the jaw 31 in its distal part.

The jaw 31 is rotatable about the support pin 45 between a separate position where the jaw 31 is separate from the energy output member 21 as illustrated in FIG. and a contact position where the jaw is in contact with the energy output member 21. The jaw 31 is provided with the same cover 25 as the energy output member 21 (the first grasping piece 21).

The operator can open and close the jaw 31 by rotating the handle 17 with respect to the case 15. In detail, when the operator operates the handle 17, the movable pipe 32 (see FIG. 2) inside the sheath 27 moves forward and backward along the central axis C of the sheath 27. The jaw 31 is configured to pivotally connect to the sheath 27 and housing 24, which allows the jaw 31 to open and close in response to a forward and backward motion of the sheath 27.

As illustrated in FIG. 5, the wiring section 34 is configured to connect to a heater control section 13A included in the power unit 13. The wiring section 34 is partly located inside the cable 14. As illustrated in FIG. 5, the wiring section 34 is also configured to connect the heater 33. The wiring section 34 is configured to electrically connect the below-mentioned heater 33 of the energy output member 21 to the power unit 13.

Figure 7:
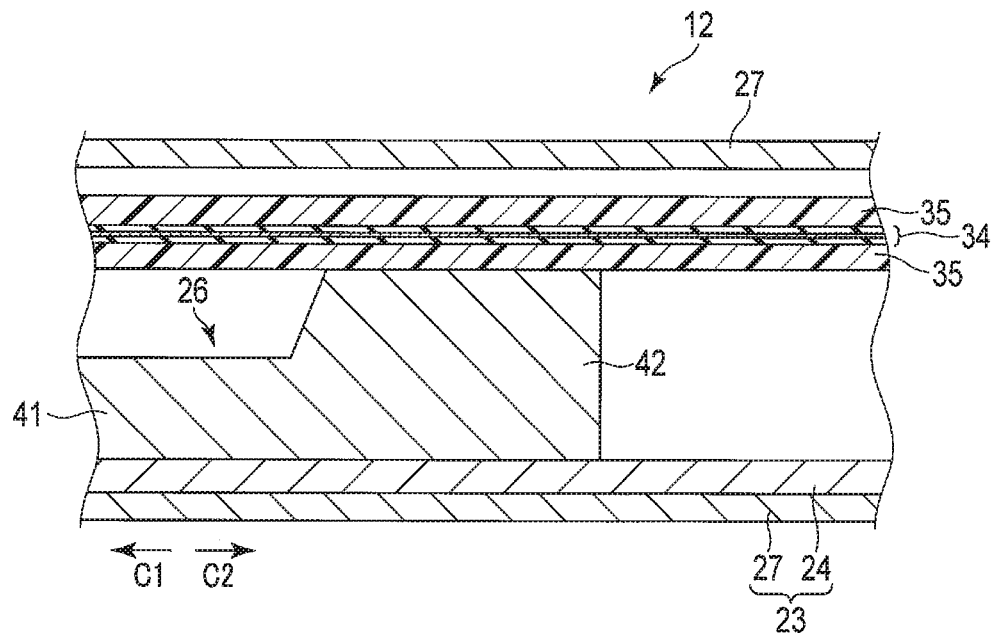
FIG. 7 is a sectional view illustrating a heatsink section in the heat conductor, housing, and wiring section illustrated in FIG. 5.

As illustrated in FIG. 7, a covering section 35 is configured to cover the wiring section 34. The wiring section 34 is composed of electric wires the surfaces of which are covered with a sheet-like insulation member. The covering section 35 is shaped like a duct, and formed integrally with the heat insulator 22 on the distal direction C1 side. Thus, the covering section 35 is made of the same material as the heat insulator 22, and has heat insulation property. The heat insulator 22 and the covering section 35 are formed integrally by insert molding the wiring section 34. The covering section 35 is in contact with the heatsink section 42 of the heat conductor 26, and is thermally connected to the heatsink section 42.

The functions of the medical device 11 according to this embodiment are described below, with reference to FIGS. 3, 5, and 6.

In the treatment, the operator can sandwich the biological tissue L between the energy output member 21 and the jaw 31 by operating the handle 17. The operator can then feed heat energy into the sandwiched biological tissue L by operating the operation button 18 in this state. The operator can thus coagulate or excise the biological tissue.

When the coagulation and incision treatment or the coagulation treatment is performed on the biological tissue (treatment object), the temperature of the energy output member 21 may become high (e.g. about 200° C. to about 300° C.). In this embodiment, the heat insulator 22 having low heat conductivity is provided between the energy output member 21 and the housing 24, so that the amount of heat transferred from the energy output member 21 to the housing 24 per unit time is reduced. Therefore, even in the case where the operator unintentionally brings the housing 24 (the back side of the energy output member 21) into contact with surrounding tissue other than the treatment site, adverse thermal effect on the surrounding tissue can be avoided.

Any heat conducted through the heat insulator 22 toward the housing 24 is conducted through the body section 41 of the heat conductor 26 to the heatsink section 42. The heat conducted to the heatsink section 42 is then conducted through the engaging section 43 in close contact with the heatsink section 42 to the housing 24. The heat conducted to the housing 24 is released toward the sheath 27. Moreover, since the housing 24 is covered with the cover 25, the possibility of adverse thermal effect on the surrounding tissue in the case where the operator unintentionally brings the housing 24 into contact with the surrounding tissue can be reduced.

According to this embodiment, a medical device 11 includes: a support member 23; an energy output member 21 that outputs energy for treating biological tissue; a heat insulator 22 provided on a back surface of the energy output member 21, and supported on a distal side of the support member 23; and a heat conductor 26 that extends over the heat insulator 22 and a part of the support member 23 more proximal than the energy output member 21, and conducts, to the support member 23, heat transferred from the energy output member 21 to the heat insulator 22.

With this structure, the heat insulator 22 covers the back surface of the energy output member 21, and so the heat of the energy output member 21 is kept from being transferred to the back side. Even in the case where the temperature of the heat insulator 22 becomes high due to extended use, the heat of the heat insulator 22 can be conducted to the support member 23 by the heat conductor 26. This suppresses the accumulation of heat in the heat insulator 22. Therefore, even in the case where the operator unintentionally brings the back side of the energy output member 21 into contact with surrounding tissue, adverse thermal effect on the surrounding tissue (heat invasion to the surrounding tissue) can be avoided.

The heat conductor 26 includes a heatsink section 42 at an end opposite to an end adjacent to the heat insulator 22. With this structure, the heat conductor 26 includes the heatsink section 42, so that the heat received from the heat insulator 22 can be actively guided to the heatsink section 42. This reduces the amount of heat accumulated in the heat insulator 22, and reduces heat invasion to the surrounding tissue.

The heat conductor 26 is thermally connected to the support member 23 through the heatsink section 42. With this structure, the heat guided to the heatsink section 42 is released toward the support member 23. This facilitates the cooling of the heatsink section 42, and lowers the temperature of the heatsink section 42. The flow of heat from the heat insulator 22 through the heat conductor 26 to the support member 23 can thus be formed. Accordingly, the heat conducted to the heatsink section 42 is kept from flowing back toward the heat insulator 22, so that the temperature around the heat insulator 22 can be further lowered.

The heat conductor 26 can include a body section 41 configured to connect the end adjacent to the heat insulator 22 and the heatsink section 42, and the heatsink section 42 has a larger volume than the body section 41. The heat conductor 26 can include a body section 41 configured to connect the end adjacent to the heat insulator 22 and the heatsink section 42, and a cross-sectional area of the heatsink section 42 along a plane intersecting a direction in which the body section 41 extends is larger than a cross-sectional area of the body section 41 along a plane parallel to the plane. With these structures, the heat capacity on the heats ink section 42 side is increased, and therefore the heat received from the heat insulator 22 can be actively guided to the heats ink section 42. By reducing the amount of heat accumulated in the heat insulator 22 in this way, the medical device 11 with low heat invasiveness to surrounding tissue can be realized.

The medical device 11 includes a housing 24 adjacent to the heat insulator 22, and the heat conductor 26 has higher heat conductivity than the housing 24. With this structure, the heat conductor 26 has high. heat conductivity than the housing 24, so that the heat transferred to the heat insulator 22 can be efficiently conducted to the support member 23 to cool the heat insulator 22 and the housing 24.

The medical device 11 includes a heat-insulation cover 25 configured to cover an outer periphery of the housing 24. With this structure, the risk of adverse thermal effect on surrounding tissue around the treatment site in the case where the operator unintentionally brings the housing 24 into contact with the surrounding tissue can be reduced.

The energy output member 21 includes: a contact section 37 that comes into contact with a treatment object; and a heater 33 that is located between the contact section 37 and the heat insulator 22, and heats the contact section 37. With this structure, heat generated from the heater 33 can be mainly conducted to the contact section 37, while preventing the conduction of heat to the heat insulator 22. This enables heating of the contact section 37 and suppresses heat loss.

The medical device 11 includes: a wiring section 34 connected to the heater 33; and a covering section 35 covering the wiring section 34 and formed integrally with the heat insulator 22. With this structure, the wiring section 34 that becomes high in temperature together with the heater 33 is covered with the covering section 35, and so the heat of the wiring section 34 can be kept from diffusing to the surroundings.

The covering section 35 is thermally connected to the heatsink section 42. With this structure, the heat of the wiring section 34 and covering section 35 is released to the heatsink section 42. As a result, malfunctions such as a fracture of the wiring section 34 caused by a temperature increase can be avoided.

Modifications of the medical device 11 are described below. The following mainly describes the differences from the foregoing embodiment, and the illustration or description of the same parts as in the foregoing embodiment is omitted.

First Modification

Figure 8:
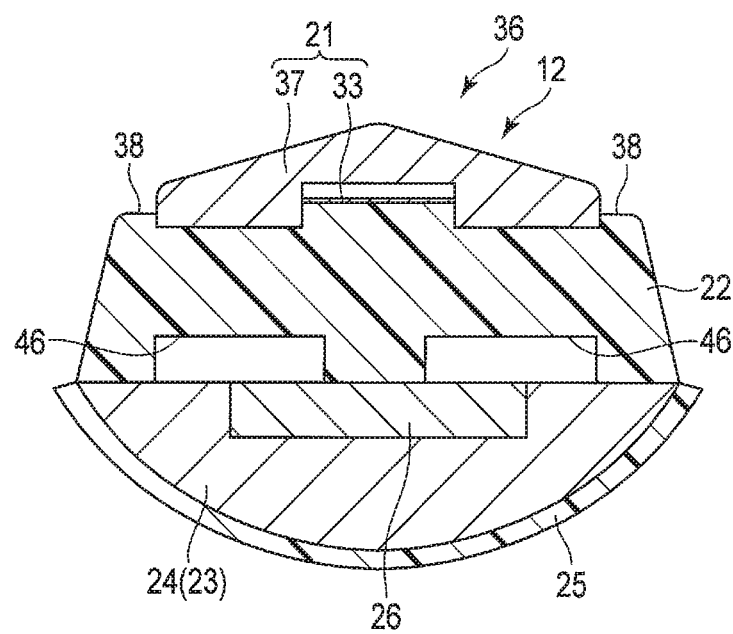
FIG. 8 is a sectional view illustrating an energy output member, heat insulator, heat conductor, and housing of a medical device according to a first modification.

A first modification of the medical device 11 is described below, with reference to FIG. 8. The heat insulator 22 has a pair of hollow parts 46 configured to extend in the central axis direction C of the sheath 27. In other words, the heat insulator 22 has a pair of grooves in the surface in contact with the housing 24, which extend in the central axis direction C of the sheath 27. A gas, such as air, a mixture of gases, a liquid, a mixture of liquids, or a mixture of one or more gases and one or more liquids is present inside the hollow parts 46. Since the hollow parts 46 in this modification enhance the heat insulation property of the end effector 36, the heat conductivity of the heat insulator 22 is further reduced.

According to the first modification, the heat insulator 22 has a hollow part 46 filled with the gas. With this structure, the heat conductivity of the heat insulator 22 is further reduced, which prevents the heat of the energy output member 21 from being directly transferred to the heat conductor 26 and the housing 24. Moreover, even in the case of using the medical device 11 under relatively harsh conditions such as long continuous use, the heat conductor 26 releases the heat of the heat insulator 22 to the support member 23. Therefore, even in the case where the operator unintentionally brings the back side of the energy output member 21 into contact with surrounding tissue other than the treatment site, adverse thermal effect on the surrounding tissue can be avoided.

Second Modification

A second modification of the medical device 11 is described below, with reference to FIG. 9. In this modification, the shape of the heatsink section 42 of the heat conductor 26 is different. The heatsink section 42 is formed as a pair of blocks configured to extend in the direction (horizontal direction) along the treatment surface of the contact section 37.

The total volume of the two parts of the heatsink section 42 can be larger than the volume of the body section 41 of the heat conductor 26. Moreover, the cross-sectional area of the heatsink section 42 along a plane intersecting the direction in which the body section 41 extends can be larger than the cross-sectional area of the body section 41 along a plane parallel to the plane.

Figure 9:
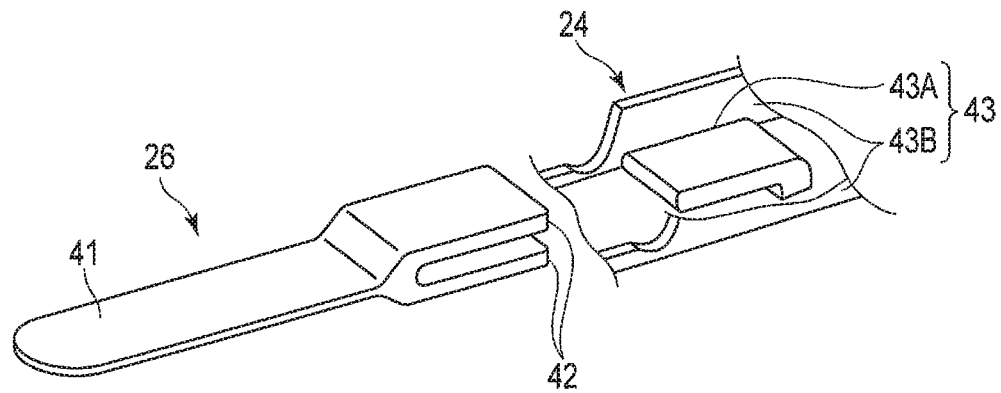
FIG. 9 is a perspective view illustrating a heat conductor of a medical device according to a second modification.

As illustrated in FIG. 9, the housing 24 includes an engaging section 43 whose shape is complementary to the shape of the heatsink section 42 of the heat conductor 26. In detail, the engaging section 43 includes: a rib section 43A sandwiched between the pair of blocks of the heatsink section 42; and a wall section 43B configured to hold the periphery of the blocks.

According to this modification, even in the case where the shape of the heatsink section 42 is different, the heat of the heat insulator 22 can be actively guided to the heatsink section 42. This further reduces the thermal effect on the surrounding tissue other than the treatment site.

Third Modification

A third modification of the medical device 11 is described below, with reference to FIG. 10. In this modification, the shape of the heatsink section 42 of the heat conductor 26 is different. The heatsink section 42 is shaped like a block having lattice-like slits 47.

The volume of the heatsink section 42 is larger than the volume of the body section 41 of the heat conductor 26. Moreover, the cross-sectional area of the heatsink section 42 along a plane intersecting the direction in which the body section 41 extends can be larger than the cross-sectional area of the body section 41 along a plane parallel to the plane.

Figure 10:
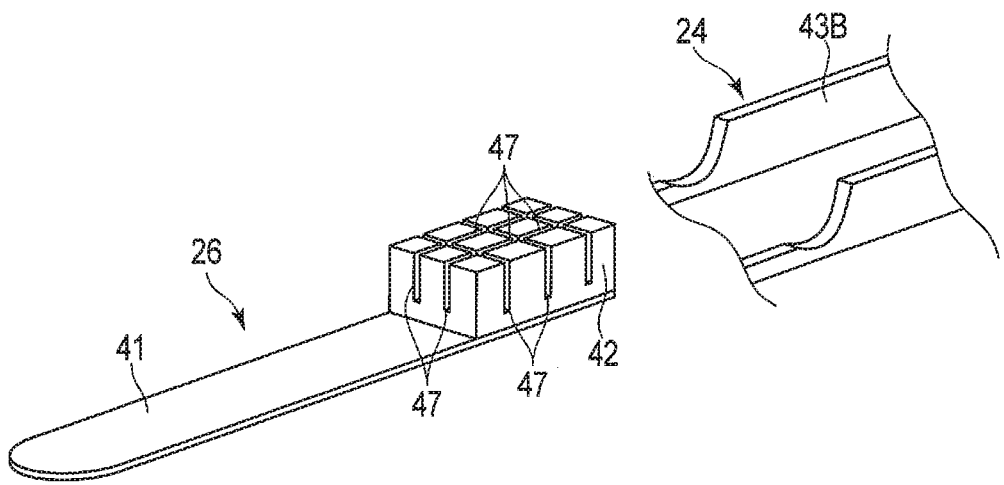
FIG. 10 is a perspective view illustrating a heat conductor of a medical device according to a third modification.

As illustrated in FIG. 10, the housing 24 includes a wall section 43B configured to hold the periphery of the heatsink section 42.

According to this modification, even in the case where the shape of the heatsink section 42 is different, the heat of the heat insulator 22 can be actively guided to the heatsink section 42. This further reduces the thermal effect on the surrounding tissue other than the treatment site.

Fourth Modification

Figure 11:
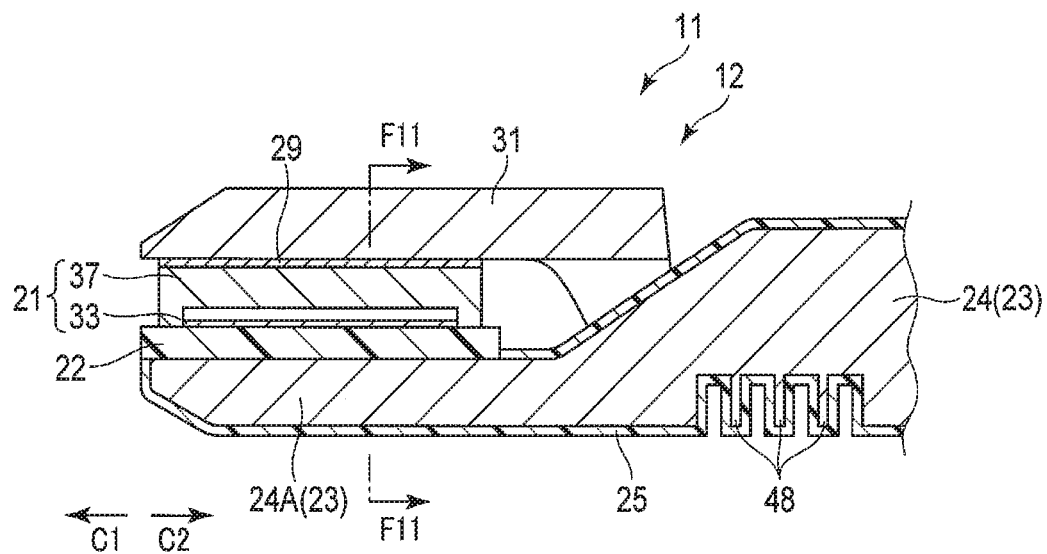
FIG. 11 is a sectional view illustrating an energy output member, heat insulator, and housing of a medical device according to a fourth modification.

A fourth modification of the medical device is described below, with reference to FIGS. 11 and 12. In this modification, the housing 24 of the support member 23 is made of a metal containing material having good heat conductivity. In more detail, the housing 24 is made of a high heat conductive material such as an aluminum alloy. The material of the housing 24 is, however, not limited to such, and may be any material having good heat conductivity. For example, the housing 24 may be made of a copper alloy or the like.

Figure 12:
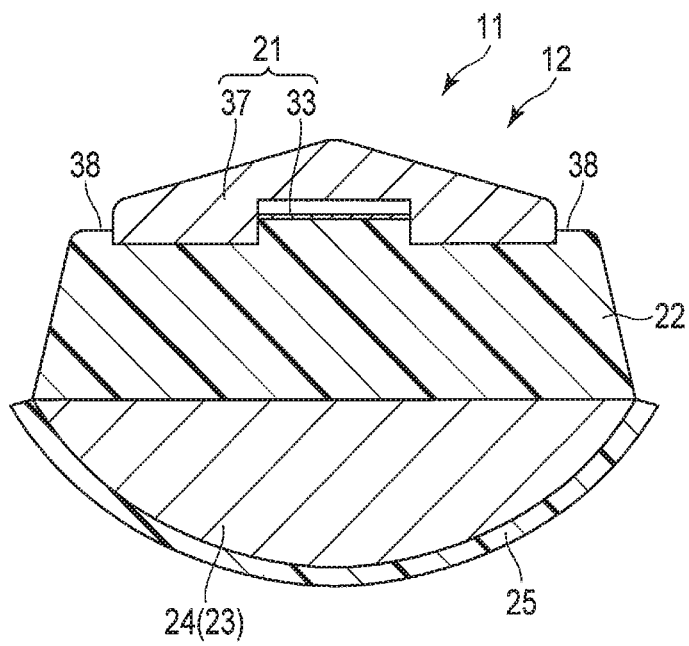
FIG. 12 is a sectional view along line F10-F10 in FIG. 11.

As illustrated in FIG. 12, the outer peripheral surface of the housing 24 is covered with the heat-insulation cover 25. The housing 24 includes a plurality of fins 48 for heat dissipation (radiation fins).

In this modification, heat transferred to the heat insulator 22 is conducted through the housing 24 toward the sheath 27 at any time. The heat is also released to the outside by the fins 48 formed in the housing 24. Hence, the temperature of the housing 24 is kept from becoming high, so that heat invasion to surrounding tissue other than the treatment site can be reduced.

The present invention is not limited to the foregoing embodiments, which may be modified as appropriate without departing from the scope of the present invention.

Although the foregoing embodiment describes the case where the energy output member 21 is provided on the first grasping piece 21 side of the end effector 36, the energy output member 21 may be provided on the second grasping piece 31 side. Moreover, the energy output member 21 is not limited to the foregoing embodiments. Other embodiments can be any other suitable member such as an electrode, an ultrasound transducer, etc.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

DESCRIPTION OF REFERENCE NUMERALS 11 medical device
21 energy output member
22 heat insulator
23 support member
24 housing
25 cover
26 heat conductor
33 heater
34 wiring section
35 covering section
37 contact section
38 outer edge section
41 body section
42 heatsink section
46 hollow part
48 fin

The invention claimed is:

1. A medical device comprising:
a support member comprising a sheath and a housing, the housing fixed to a distal end of the sheath;
a heat insulator provided on at least a portion of a first surface of the housing;
an energy output member configured to output an output energy, the energy output member provided on at least a portion of a first surface of the heat insulator, the output energy configured to treat biological tissue, wherein the energy output member comprises:
a contact surface that is configured to contact an object to be treated; and
a heater located between the contact surface and the heat insulator, the heater configured to heat the contact surface;
a wire connected to the heater;
a cover configured to cover at least a portion of the wire, the cover in contact with a portion of the heat insulator, wherein the cover is connected to the heatsink;
a heat-insulation cover configured to cover at least a portion of an outer periphery of the housing; and
a heat conductor provided on at least a portion of the first surface of the housing and contacting a second surface of the heat insulator, the second surface of the heat insulator opposite the first surface of the heat insulator, wherein, the heat conductor having greater heat conductivity than the housing, wherein the heat conductor comprises a distal end portion and a proximal end portion, the proximal end portion of the heat conductor comprising a heatsink,
a portion of the sheath is located proximal to the energy output member, and
the energy output member is configured to transfer heat to the heat insulator, and wherein the heat conductor is configured to conduct the heat from the heat insulator to the sheath.

2. The medical device according to claim 1, wherein the heatsink contacts a portion of the housing.

3. The medical device according to claim 2, wherein the distal end portion of the heat conductor comprises a body section connected to the proximal end portion, and
wherein the heatsink has a larger volume than the body section.

4. The medical device according to claim 2, wherein the distal end portion of the heat conductor comprises a body section that connects to the proximal end portion, and
wherein a cross-sectional area of the heatsink along a plane intersecting a longitudinal axis of the medical device is larger than a cross-sectional area of the body section along a plane parallel to the plane.

5. The medical device according to claim 1, wherein the heat insulator forms a hollow portion in an area adjacent the second surface of the heat insulator.

6. The medical device according to claim 1, wherein the heat insulator comprises an outer edge section located along an outer periphery of the energy output member that extends further than the outer periphery of the energy output member.

7. A medical device comprising:
a support member;
a heat insulator provided on at least a portion of a first surface of the support member;
an energy output member configured to output an output energy, the energy output member provided on at least a portion of a first surface of the heat insulator, the output energy configured to treat biological tissue, wherein the energy output member comprises a contact surface that is configured to contact an object to be treated, and a heater located between the contact surface and the heat insulator, the heater configured to heat the contact surface;
a wire connected to the heater;
a cover configured to cover at least a portion of the wire, the cover in contact with a portion of the heat insulator; and
a heat conductor comprising a distal end portion and a proximal end portion, the proximal end portion of the heat conductor comprising a heatsink, the heat conductor provided on at least a portion of the first surface of the support member and contacting a second surface of the heat insulator, the second surface of the heat insulator opposite the first surface of the heat insulator, wherein, a portion of the support member is located proximal to the energy output member, and the energy output member is configured to transfer heat to the heat insulator, and wherein the heat conductor is configured to conduct the heat from the heat insulator to the support member, and wherein the cover is connected to the heatsink.

8. The medical device according to claim 7, wherein the heatsink contacts a portion of the support member.

9. The medical device according to claim 8, wherein the distal end portion of the heat conductor comprises a body section connected to the proximal end portion, and wherein the heatsink has a larger volume than the body section.

10. The medical device according to claim 7, wherein the distal end portion of the heat conductor comprises a body section that connects to the proximal end portion, and wherein a cross-sectional area of the heatsink along a plane intersecting a longitudinal axis of the medical device is larger than a cross-sectional area of the body section along a plane parallel to the plane.

11. The medical device according to claim 7, wherein the heat insulator forms a hollow portion in an area adjacent the second surface of the heat insulator.

12. The medical device according to claim 7, wherein the heat insulator comprises an outer edge section located along an outer periphery of the energy output member that extends further than the outer periphery of the energy output member.

13. The medical device according to claim 7, comprising a housing adjacent to the heat insulator, wherein the heat conductor comprises higher heat conductivity than the housing.

14. The medical device according to claim 13, comprising a heat-insulation cover configured to cover at least a portion of an outer periphery of the housing.

\* \* \* \* \*